United States Patent
Kumar et al.

(10) Patent No.: US 7,629,465 B2
(45) Date of Patent: Dec. 8, 2009

(54) INDUSTRIAL PROCESS FOR PREPARATION OF CLOPIDOGREL HYDROGEN SULPHATE

(75) Inventors: Ashok Kumar, Maharashtra (IN); Ketan Dhansukhlal Vyas, Maharashtra (IN); Sanjay Govind Barve, Maharashtra (IN); Priti Jayesh Bhayani, Maharashtra (IN); Sanjay Nandavadekar, Maharashtra (IN); Chirag Hasmukh Shah, Maharashtra (IN); Sandeep Madhavrao Burudkar, Maharashtra (IN); Lavkesh Dayashankar Kushwaha, Maharashtra (IN)

(73) Assignee: IPCA Laboratories Ltd., Mumbai (IN)

( * ) Notice: Subject to any disclaimer, the term of this patent is extended or adjusted under 35 U.S.C. 154(b) by 168 days.

(21) Appl. No.: 10/591,657

(22) PCT Filed: Mar. 4, 2005

(86) PCT No.: PCT/IN2005/000071

§ 371 (c)(1),
(2), (4) Date: Sep. 5, 2006

(87) PCT Pub. No.: WO2005/104663

PCT Pub. Date: Nov. 10, 2005

(65) Prior Publication Data

US 2008/0097101 A1    Apr. 24, 2008

(30) Foreign Application Priority Data

Mar. 5, 2004    (IN) .................. 281/MUM/2004
Jun. 4, 2004    (IN) .................. 626/MUM/2004
Aug. 10, 2004   (IN) .................. 861/MUM/2004

(51) Int. Cl.
*C07D 471/02* (2006.01)
(52) U.S. Cl. ....................................... 546/114
(58) Field of Classification Search .............. 546/114
See application file for complete search history.

(56) References Cited

U.S. PATENT DOCUMENTS 6,635,763 B2 * 10/2003 Pandey et al. ............... 546/114
6,767,913 B2 *  7/2004 Lifshitz et al. .............. 514/301

OTHER PUBLICATIONS

Bernstein "Polymorphism in moleciar crystals" Oxford:Clarendon Press 115-118,272 (2002).*

* cited by examiner

*Primary Examiner*—Patricia L Morris
(74) *Attorney, Agent, or Firm*—Blank Rome LLP

(57) ABSTRACT

An improved process for the manufacture of Clopidogrel starting from 2-(2-thienyl) ethylamine, which eliminates the isolation of an unstable intermediate like 2-(2-thienyl) ethyl formimine by subjecting it to a one pot cyclization to get 4, 5, 6, 7-tetrahydrothieno (3,2-c) pyridine of Formula II and further reacting with halo-compound of Formula III (where X is Cl or Br) at 20 to 90° C. temperature characterized in a solvent like water and/or dichloroethane in presence of organic or inorganic bases is disclosed herein. This invention further discloses a process for resolution of racemic Clopidogrel into its optical antipodes and converting the dextroclopidogrel base into its known polymorphs namely 'Form I' or 'Form II' in solvents selected from methyl propyl ketone, methyl isopropyl ketone, diethyl ketone or their mixture thereof, mixture of ethyl acetate and methyl propyl ketone, mixture of ethyl acetate and methyl isopropyl ketone, or mixture of ethyl acetate and diethyl ketone or ethyl acetate.

12 Claims, 8 Drawing Sheets

INDUSTRIAL PROCESS FOR PREPARATION OF CLOPIDOGREL HYDROGEN SULPHATE

TECHNICAL FIELD OF INVENTION

The present invention relates to an improved process for manufacturing (+)-(S)-alpha-(2-chlorphenyl)-6,7-dihydrothieno [3,2-c] pyridine-5 (4-H)-acetic acid methyl ester of Formula I, commonly known as Clopidogrel starting from 2-(2-thienyl) ethylamine. The present invention further relates to the process for resolution of the racemic clopidogrel into its optical antipodes with high chiral purity. The present invention also provides a reproducible process for production of hydrogen sulphate salt of clopidogrel in two crystalline forms viz: Form-I and Form-II.

BACKGROUND OF THE INVENTION (+)-(S)-alpha-2-(chlorphenyl)-6,7-dihydrothieno [3,2-c] pyridine-5 (4-H)-acetic acid methyl ester known as clopidogrel under the International Non-Proprietry Name is marketed as hydrogen sulphate salt. Clopidogrel is known for its platelet aggregating and antithrombotic properties and finds medicinal applications in this field. It can be represented by Formula-I, and was disclosed in U.S. Pat. No. 4,529,596 (hereinafter referred as '596' patent) in its racemic form for the first time.

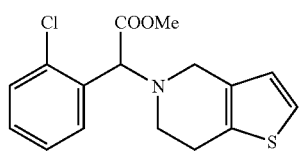

Formula I

The '596' patent provides a synthesis of said molecule of Formula I by the reaction of a thienopyridine derivative of Formula II with a chloro compound of Formula III (where X=Cl) in solvents like dimethyl formamide, alcohols and ethyl acetate in presence of alkali metal carbonates. However, it does not suggest preparation/source of the starting material, tetrahydrothienopyridine derivative, of Formula II.

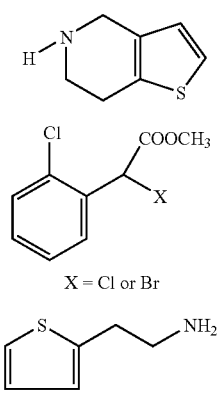

X = Cl or Br

In a subsequent patent, JP 63101385, a convenient process for the preparation of the 4,5,6,7-tetrahydrothieno (3,2-c) pyridine intermediate (Formula II) was disclosed. According to the multi-step process of this patent, a commercially available 2-(2-thienyl)-ethylamine (Formula IV) was reacted with formaldehyde to give an intermediate 1,3,5-tris-(2-thienyl-ethyl)-hexahydro-S-triazine which was isolated and treated with HCl in polar solvents to give the 4,5,6,7-tetrahydrothieno (3,2-c) pyridine of Formula II.

A similar process was disclosed in U.S. Pat. No. 5,132,435 for the preparation of Clopidogrel by using the same reactants per se to yield the 4,5,6,7-tetrahydrothieno (3,2-c) pyridine derivative (Formula II) and reacting the same with a bromo-derivative of Formula III (X=Br) in solvents selected from alcoholic solvents, DMF, ether solvents and ethyl acetate in presence of alkali metal carbonate as the base. In the process, 2-(2-thienyl) ethylamine was reacted with formalin solution in water by heating to a temperature range of 70° C. to 90° C. and isolated the 2-(2-thienyl)-ethyl formimine by a long procedure in pure form. This was reacted with dry hydrochloric acid solution in dimethylformamide to form the cyclized product (Formula II).

In these processes the reactants per se are same but employ varying conditions to achieve better purity or yield. Although some of the problems are solved by modifying the reaction conditions or route of synthesis as taught by the prior art, there still exist problems like polymerization of intermediates which need to be investigated.

The cyclisation of the intermediate 2-(2-thienyl)-ethyl formimine does not take place in presence of water. If water is present in the reaction it necessitates the isolation of formimine intermediate in pure form. This increases the number of operations and makes process plant unfriendly from industrial scale-up point of view. Moreover, the isolated intermediate, 2-(2-thienyl) ethyl formimine, is not a stable compound and polymerizes to give a trimer which makes it difficult to store/handle in normal conditions.

Although, the reaction of bromo-compound (Formula III) with 4,5,6,7-tetrahydrothieno (3,2-c) pyridine of Formula II gave moderate yields in the reported processes, the reactions takes long time for completion at temperature 60° C. to 90° C. as reported in '435' patent.

Carrying out reactions at above temperatures, that too for longer period, lead to formation of various impurities due to the lack of selectivity of reactions or decomposition of the reactants or products, which necessitates extra purification resulting into yield losses and increase in number of operations not desirable for a practical process. The search for a manufacturing process for the preparation of Clopidogrel employing easy synthetic methods resulting in a satisfactory yield/purity of final product remains undoubtedly of interest.

The pure enantiomeric forms of clopidogrel (dextro and levo isomers) was disclosed in EP 281459 which teaches the isolation of the dextro rotatory isomer of Clopidogrel by diasteriomeric salt formation of racemic Clopidogrel base using an optically active acid such as 10-L-camphor sulfonic acid in solvents like acetone, followed by successive recrystallization of the salt until a product with constant rotatory power was obtained. The pure dextrorotatory isomer of clopidogrel ( herein after referred as clopidogrel free base) was released from the respective diasteriomeric salt by reaction with a base.

But in practice, the diasteriomeric salt that separates out was filtered, and purified by refluxing, cooling and filtration from acetone results in low yield of the dextro isomer (55%). The process of purification in acetone is repeated several times for obtaining the desired purity of diasteriomeric salt. The chiral purity of the dextroisomer is low (96%) even after the repeated crystallization.

The Clopidogrel free base was then converted into its hydrogen sulfate salt by dissolving in acetone, cooling and mixing with concentrated sulfuric acid to precipitation. The precipitate thus obtained is then isolated by filtration, washed and dried to give Clopidogrel hydrogen sulfate in the form of white crystals whose melting point was 184° C. and optical rotation was +55.1° (c=1.891/CH3OH). But '459 patent did not characterize or suggest any name to this crystals (polymorph) of Clopidogrel hydrogen sulfate.

Subsequently International patent publication, WO 99/65915 (herein after referred as '915 patent), disclosed two polymorph forms of Clopidogrel hydrogen sulfate referred to as Form-I and Form-II. The '915 patent identified that the precipitation method described in '459 patent had led to crystalline Form-I. The '915 also deals with a new crystalline form called Form-II of Clopidogrel hydrogen sulfate. The latter is suggested to be thermodynamically most stable crystalline form. According to '915 patent both polymorphs, namely Form I and Form II, were prepared from the same solvent viz; acetone.

The process for obtaining crystalline Form-II of Clopidogrel hydrogen sulfate according to example 1A of the '915 patent describes the introduction of Clopidogrel camphor sulfate in MDC and transformation of salt into the base with potassium carbonate solution. Clopidogrel base is extracted in MDC and evaporated. Residue obtained is dissolved in acetone and cooled. Addition of sulfuric acid precipitated out Clopidogrel hydrogen sulfate. Also in the same application it was described to get Form-II either by keeping mother liquor of Form-I or by heating acetone solution containing the base after addition of sulfuric acid to reflux or by subjecting the suspension to mechanical shearing using a shearing device or by inoculation.

However, this process was not suitable for the production of Form I of clopidogrel hydrogen sulphate on an industrial scale owing to its thermodynamic instability in solvents like acetone and invariably yielded Form II without having the need of keeping for longer periods (ref. '915 patent). This problem became the subject of the patent application WO 2004020443 (herein after referred as '443 patent).

According to the '443 patent application, a process was claimed to produce Form I consistently by forming hydrogen sulphate salt of clopidogrel from a solvent selected from the series of $C_1$-$C_5$ alcohols or their esters with $C_1$-$C_4$ acids, optionally of mixture of alcohols and esters. The process involves dissolving clopidogrel base in solvents like isopropyl alcohol and/or butyl acetate, cooling the mixture, adding sulfuric acid and inoculating the mixture with Form-I of Clopidogrel hydrogen sulfate. Stirring the crystallized mixture precisely at a temperature between –5 and +15° C. to get crystals of clopidogrel in Form-I. In another process variant, the subject of '443 patent, the clopidogrel hydrogen sulphate was directly dissolved at reflux in the above mentioned solvents and crystallized under cooling.

Although the process mentioned in the '443 patent application works in butyl acetate, which is known to have hazardous properties (affects central nervous system and exposure limit is 150 ppm), but fails to give pure Form I in other industrially friendly solvents like ethyl acetate under the specified conditions. As the Form I is thermodynamically unstable, the process variant of dissolving clopidogrel hydrogen sulphate salt in solvents at higher temperature and cooling to precipitate Form I resulted in Form II or Form IV or their mixture with Form I.

This finding is in agreement with the prior art disclosed in United States patent application 2003/0225129 $A_2$ (herein after referred as '129 patent), where isopropanol was used to produce Form-IV crystals (Form IV of clopidogrel hydrogen sulphate is known to be its isopropyl alcohol solvate) by a process comprising the steps of preparing solution of Clopidogrel hydrogen sulfate either by using Clopidogrel base or its hydrogen sulfate salt in isopropyl alcohol at reflux and cooling to precipitate Clopidogrel hydrogen sulfate and separating the mentioned polymorph, i.e. Form IV.

The '129 patent also describes process for the preparation of Form-II from solvents selected from dichloromethane, 1,4-dioxane, toluene, chloroform, ethyl acetate, methyl ethyl ketone and t-butyl methyl ether. The '129 patent, for the first time, claimed to produce Form II from ethyl acetate which was the main subject of '443 patent application.

Moreover, in our hands under the specified conditions at lower temperature of –5° to 15° C., as claimed in the '443 patent, we found the crystals formed in ethyl acetate is Form II of clopidogrel hydrogen sulphate.

It is clear from above discussion that same solvent gives two different crystalline forms under different experimental conditions.

So, it is evident from the prior art that methods to produce Form-I of clopidogrel hydrogen sulphate from different solvents are poorly reproducible, necessitating the optimization of experimental conditions other than of the selection of solvents. Since Form-I is kinetically controlled and Form-II is thermodynamically controlled form, they require very specific temperature range and specific conditions for getting reproducible results. Also, a minor variation in condition appears to give Form-II instead of expected Form-I or a mixture of Form-I & Form-II. Since, Form I of clopidogrel hydrogen sulphate is used for pharmaceutical formulation, the importance of a rugged method that gives Form I consistently doesn't require any emphasis.

Apart from the inconsistency of the process in solvents like ethyl acetate, the process given in the '443 patent application also suffers from operational problems from an industrial scale-up point of view as follows;

1. During the salt formation in solvents like ethyl acetate at lower temperature, the product forms a sticky & lumpy mass that sticks to the stirrer and difficult to disperse due to the lowered solubility at this condition,
2. The workability of the process found limit to single solvent mainly butyl acetate which is a hazardous and industrially unfriendly,
3. The crystal form obtained by performing the salt formation between 5° to 15° C. in ethyl acetate is Form II of clopidogrel hydrogen sulphate. This may be due to the non-dispersability of the sticky mass obtained under these conditions and the fast/prolonged stirring performed for dispersion, allows the crystals to grow and rearranges to the most stable form.

Thus there is a need to get industrially reliable process for the preparation of Form-I and Form-II without contamination of one into other Form. So it was of interest to find a suitable solvent where the crystallization can be performed at a temperature near to ambient temperature, for solving the inconsistency/operational problems in the prior art, yielding clopidogrel Form I in its pure state. Also of interest was to see its workability at higher temperature to affect a fast and easily dispersible crystallization conditions, an important factor for operations.

OBJECTIVES OF THE PRESENT INVENTION

It is, therefore, an objective of the present invention to provide an industrially useful process for the manufacture of Clopidogrel from starting materials that are readily and commercially available, relatively inexpensive, and easily maneuvered at large scale operations.

Other objectives of this invention are
1. to provide a single pot conversion process for unstable intermediate 2-(2-thienyl)ethyl formimine formed in the reaction to a stable product of Formula II.
2. to design a process for preparation of Clopidogrel wherein the condensation of halo ester with 4,5,6,7-tetrahydrothieno (3,2-c) pyridine is performed under ambient conditions with accelerated rate of reaction.
3. to provide, optionally, a one-pot processes for the preparation of racemic Clopidogrel starting from 2-(2-thienyl)ethylamine.
4. To provide suitable solvents for resolving racemic clopidogrel base into substantially pure enantiomers in a single diasteriomeric fractional separation step in higher outputs.

A further objective of the present invention was to find solvent systems where the Form I crystals of clopidogrel hydrogen sulphate can be efficiently and reproducibly formed on industrial scale. These objectives become the subject of the present invention.

SUMMARY OF THE INVENTION

Accordingly, in a first aspect, there is provided an improved process for the manufacture of Clopidogrel starting from 2-(2-thienyl) ethylamine, which eliminates the isolation of an unstable intermediate like 2-(2-thienyl) ethyl formimine by subjecting it to a one pot cyclization to get 4,5,6,7-tetrahydrothieno (3,2-c) pyridine of Formula II.

In one embodiment of the present invention, the 4,5,6,7-tetrahydrothieno (3,2-c) pyridine is reacted with halo-compound of Formula III (where X is Cl or Br) at room temperature in a solvent like water and/or ethylene dichloride (EDC) in presence of organic or inorganic bases like sodium carbonate.

In preferred embodiment of the invention, the 2-(2-thienyl) ethylamine is reacted with paraformaldehyde in solvents such as hydrocarbon solvents including aliphatic, aromatic and chlorinated hydrocarbon solvents and removing the water formed, azeotropically during reaction. The 2-(2-thienyl) ethyl formimine solution is cyclized in a single pot by supplying dry HCl gas/solution.

In yet another embodiment, the reaction of Formula II with Formula III is carried out in a combination of solvents like water and chlorinated hydrocarbon solvents at room temperature.

In yet another embodiment, the production of Clopidogrel is carried out in a single pot by reacting 2-(2-thienyl) ethylamine with paraformaldehyde in organic solvents, azeotropically removing water formed in the reactor, cyclizing the 2-(2-thienyl) ethyl formimine by supplying dry HCl gas/solution, and reacting the 4,5,6,7-tetrahydrothieno (3,2-c) pyridine formed with a solution of haloester (Formula III, where X=Cl or Br) in water or organic solvent or their mixtures thereof in presence of a base.

In a second aspect of the present invention, a racemic resolution of(±)methyl 2-(2-chlorophenyl)-2-(4,5,6,7-tetrahydrothieno[3,2-c]pyridin-5-yl) acetate to get substantially pure dextro rotatory enantiomer methyl-(S)-(+)-2-(2-chlorophenyl)-2-(4,5,6,7-tetrahydrothieno[3,2-c]pyridin-5-yl) acetate (Formula IA) using anhydrous levo-camphor-10-sulphonic acid in a mixture of solvents selected from combination of polar and non-polar/weakly polar solvents like acetone:dichloromethane, acetone:toluene, and acetone:cyclohexane is provided.

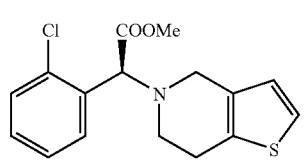

Formula IA

In a third aspect, the present invention provides an improved industrial process for crystallizing out polymorph 'Form I' of(+)clopidogrel hydrogen sulphate (also called clopidogrel hydrogen sulphate) in solvents such as methyl propyl ketone, methyl isopropyl ketone, diethyl ketone or their mixture thereof, ethyl acetate, mixture of ethyl acetate and methyl propyl ketone, mixture of ethyl acetate and methyl isopropyl ketone, mixture of ethyl acetate and diethyl ketone, in a reproducible manner without detectable contamination of 'Form II'.

In a preferred embodiment of the present invention the process for 'Form I' comprises dissolving the clopidogrel base in solvent such as methyl propyl ketone or methyl isopropyl ketone or diethyl ketone or mixture of ethyl acetate and methyl propyl ketone or mixture of ethyl acetate and methyl isopropyl ketone, mixture of ethyl acetate and diethyl ketone at room temperature (20 to 30° C.), then cooling the obtained clopidogrel base solution to a temperature of −10 to 10° C., adding concentrated sulphuric acid (98%, d=1.84) while maintaining the temperature in the range −10 to 20° C., further maintaining the temperature at about 10 to 30° C. for about 12 to 17 hours and filtering the crystals of Form I obtained.

In another embodiment, present invention provides a process for 'Form I' clopidogrel hydrogen sulphate in ethyl acetate, in a reproducible manner without detectable contamination of Form-II at a temperature ranging from 18° to 30° C. in a duration of 8 to 10 hours. The present invention also provides process for the formation of clopidogrel Form II from ethyl acetate at a temperature of 45° C. to 50° C. without detectable contamination of Form I.

The present invention provides process for preparation of both Form-I and Form-II from the same solvent, i.e. ethyl acetate, at different experimental condition, which gives operation-wise flexibility and excellent reproducibility, making the process practical and plant friendly.

In a further embodiment, the present invention provides a process for the preparation of 'Form II' clopidogrel hydrogen sulphate from a commonly used solvent like isopropanol and tetrahydrofuran.

DETAILED DESCRIPTION OF THE INVENTION

Figure 1:
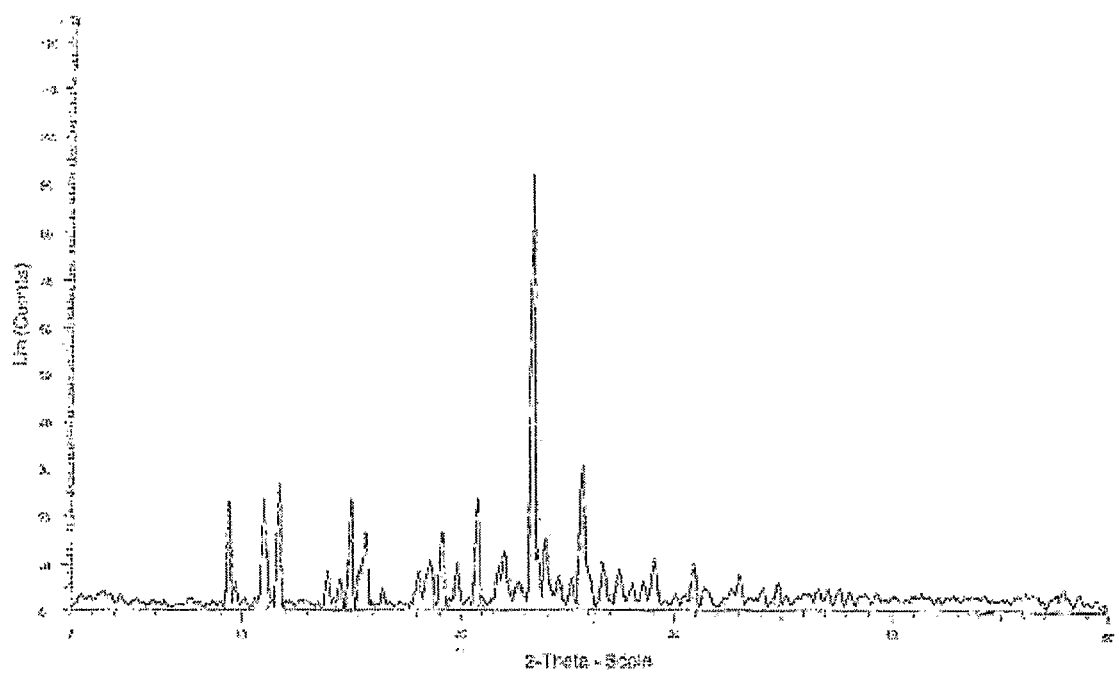
FIG. 1 represents Powder X-Ray diffraction pattern (PXRD) of clopidogrel hydrogen sulphate Form I prepared according to example 7 of the present invention.

The improved process for preparation of racemic clopidogrel, its resolution, and conversion to hydrogen sulphate salt in specific crystalline forms viz; 'Form I' and 'Form II' are described in detail with the specific embodiments/conditions here after.

It has now been found that new condition/process makes it possible to convert 2-(2-thienyl) ethylamine to 4,5,6,7-tetrahydrothieno (3,2-c) pyridine via 2-(2-thienyl) ethyl formimine in a single step in one-pot and thereby eliminating the isolation of unstable intermediate, 2-(2-thienyl) ethyl formimine, making the process industrially more feasible.

Consequently, the invention relates to an improved synthesis of Clopidogrel by reacting 2-(2-thienyl) ethylamine with paraformaldehyde in presence of dry HCl, optionally isolating the compound of Formula II, and reacting with halo-compound of Formula III (X=Cl or Br) in a single organic solvent or a combination of organic solvents and water.

Accordingly, the 2-(2-thienyl) ethylamine is reacted with paraformaldehyde in a suitable solvent selected from non-polar solvent like aliphatic and aromatic hydrocarbon solvents, chlorinated hydrocarbons like dichloroethane (EDC) etc. The reaction takes place at a temperature of 30° C. to 100° C. and the water formed as a byproduct in the reaction is removed continuously by azeotropic distillation using a Dean-Stark assembly or the like. Azeotropic distillation herein means removal of two or more solvents from a mixture of solvents that form a low boiling mixture called azeotrope by distillation at elevated temperature.

After removal of water, the intermediate 2-(2-thienyl) ethyl formimine formed in solution is in situ reacted with dry HCl gas. The dry HCl also can be advantageously introduced into reactor as a solution in a suitable organic solvent. The solvent used for this purpose include dimethyl formamide, alcoholic solvents like methanol, ethanol, isopropyl alcohol etc. The one pot conversion of 2-(2-thienyl) ethylamine takes place in a period of 4 to 8 hours. The preferred temperature for carrying out the cyclization of intermediate in presence of the acid catalyst is in the range from 60° C. to 90° C.

According to present invention, the cyclization of 2-(2-thienyl) ethyl formimine obtained takes place in-situ spontaneously in presence of acid and yields the stable intermediate 4,5,6,7-tetrahydrothieno (3,2-c) pyridine as its hydrochloride salt. The said salt precipitates from the reaction medium and conveniently isolated in substantially pure form.

The acid catalyzed cyclization of 2-(2-thienyl) ethyl formimine is preferably carried out at a temperature range of 70° C. to 75° C., for a period of 4 hours.

According to a preferred embodiment of the invention, the 4,5,6,7-tetrahydrothieno (3,2-c) pyridine as a free base or its hydrochloride salt form is reacted with a halo derivative of Formula III in organic solvent especially dichloroethane in presence of an organic base to obtain Clopidogrel. The organic base for carrying out this step of the process is selected from the group consisting of trialkyl amines such as triethylamine, trimethylamine, diisopropylethylamine and the like. The preferred base is triethylamine. The preferred halo derivative of Formula III is the bromo compound (Formula III, where X=Br).

According to the above process step of the present invention, wherein the compound III and 4,5,6,7-tetrahydrothieno (3,2-c) pyridine is reacted, the reaction is carried out at a temperature range of about 50° C. to about 80° C. for about 4 to 4.5 hours, preferably about 3.5 hours at 70° C. In this step of the process, where the acid salt of Formula II is used as reactant, then an excess amount of the base is used. This is required to neutralize the acid salt to liberate the free base of the compound of Formula II that reacts with the halo derivatives of Formula III.

In another embodiment of the invention, the process step of reaction of 4,5,6,7-tetrahydrothieno(3,2-c)pyridine with the halo compound of Formula III is carried out in a heterogeneous mixture of solvents selected from a combination of water and chlorinated hydrocarbon solvents such as dichloromethane or dichloroethane. The preferred solvent is a mixture of water and dichloroethane. The preferred ratio of water and dichloroethane is 1:0.5. A specific advantage of this reaction medium is that a phase-transfer catalyst as taught by prior patents is not required and the reaction can be performed at ambient conditions.

The base for carrying out the above process step is selected from the group consisting of inorganic bases like alkali metal carbonates. The preferred alkali metal carbonate used is sodium carbonate or potassium carbonate.

Preferably the inorganic base may be used in molar equivalent ratio relative to the halo compound of Formula III or in slight excess. In the case of reaction of acid salt of Formula II with Formula III, an excess base is used to liberate the free amine from acid salt. A preferable ratio of base used in this case ranges from 2 moles to 3 moles relative to compound of Formula II.

In this step of the process, the 4,5,6,7-tetrahydrothieno(3,2-c)pyridine or its hydrochloride salt and the inorganic base is preferably taken in water in a reaction vessel. The addition of a compound of Formula III is carried out as its solution in dichloroethane to form the heterogeneous reaction conditions. This process is particularly advantageous from the point of view of handling the halo compound of Formula III, due to its highly irritant and lachrymator properties.

According to the process of the present invention, this step is advantageously carried out at ambient temperature. Although the reaction goes faster at high temperature, to limit the impurity generation, this step is carried out at a temperature of 25° C. to 30° C. for a period of 7 to 10 hours, preferably 10 hours.

The Clopidogrel prepared following the above method is isolated by phase separation and washing the organic layer with water. The organic layer is removed by evaporation and the clopidogrel base obtained is purified in acetone by making its hydrogen sulphate salt. The pure Clopidogrel hydrogen sulphate is isolated as pure crystals from the solvent by suction filtration and drying.

According to a particularly advantageous alternative form of the present invention, the preparation of Clopidogrel may be carried out from 4,5,6,7-tetrahydrothieno (3,2-c) pyridine intermediate in the actual medium (hydrocarbon solvents) in which it is prepared in a single pot.

Consequently, according to the invention, clopidogrel is prepared by the following reactions in a single pot.

1. 2-(2-thienyl)ethylamine is reacted with paraformaldehyde in suitable solvent as described earlier and removing the water formed in the reaction azeotropically.
2. introducing dry HCl in the form of solution or gas and cyclizing the corresponding formimine to give 4,5,6,7-tetrahydrothieno(3,2-c)pyridine as hydrochloride salt in the reaction vessel.
3. saponifying the hydrochloride salt of 4,5,6,7-tetrahydrothieno(3,2-c)pyridine of Formula II with introduction of an aqueous solution of sodium or potassium carbonate in required amounts.
4. introducing halo-compound of Formula III as such or as a solution in organic solvent used for the stage 1 and reacting at a temperature of 25° C. to 30° C. for a period of 8 to 10 hours, preferably 10 hours,
5. isolating the Clopidogrel base in the organic layer after phase separation and washing with water, removing the solvent by evaporation to leave Clopidogrel base as residue in the reaction vessel, and
6. isolating pure Clopidogrel hydrogen sulphate by introducing acetone and conc. sulphuric acid into the reaction vessel.

The addition of Sulphuric acid is carried out preferably at a temperature of 0° C. to 25° and the addition of Sulphuric acid to the acetone solution of Clopidogrel base may be carried out in a controlled manner so as to avoid undue exothermicity with proper cooling. The hydrogen sulphate salt was further treated with a base like sodium or potassium carbonate to liberate the free clopidogrel base.

The Clopidogrel base obtained by the process of the present invention is, further, resolved into its enantiomers using optically active camphorsulphonic acid. The process of resolution involves contacting Clopidogrel base with (−)camphor sulphonic acid in a mixture of polar and non-polar/weakly polar organic solvents and crystallizing the dextroisomer as a diasteriomeric salt of camphor sulphonic salt.

The solvent of choice used in preparing combination solvents is selected from acetone, dichloromethane, toluene and cyclohexane. The mixtures of solvents ideal for resolution of racemic clopidogrel are combination of acetone:dichloromethane, acetone:toluene, and acetone:cyclohexane; wherein the preferred mixtures of the solvents are combination of acetone:dichloromethane and acetone:toluene, and the most preferred mixture of the solvents is acetone:dichloromethane. This solvent combination in a preferred proportion is essential for the success of resolution in respect of yield and purity in a single crystallization step. The preferred ratio of the solvents used is 20:0.5 (10:0.25), wherein the more preferred ratio is 15:0.75 and the most preferred ratio is 10:1. It is preferable to use anhydrous levo-camphor-10-sulphonic acid and the most preferred molar ratio of camphor sulphonic acid is 1.05 to 1.1 molar equivalents relative to the racemic clopidogrel mixture. The salt formation is carried out in the temperature range of 25-35° C., preferably at 30±2° C.

The diasteriomer salt is then hydrolyzed using alkali metal carbonates such as sodium carbonate or ammonia to liberate the dextro enantiomer of Clopidogrel as free base. After hydrolysis, (+)(S) Clopidogrel base was isolated by extraction using organic solvents like dichloromethane followed by evaporation of solvent to give (+) Clopidogrel having an enantiomeric purity more than 99.5% with an yield of 76 to 80%.

Owing to the economy of the process, the unwanted isomer, (−)(R) clopidogrel camphor sulphonate salt, left behind in the mother liquor after crystallization of S-isomer is racemized and recycled. The mother liquor containing (−)(R) clopidogrel camphor sulphonate along with some amount of unrecovered S-isomer after removal of crystallization solvent is treated with NaOH in alcoholic solvents like methanol at a temperature ranging from 30 to 50° C. to obtain a 50:50 ratio of both isomers (referred as racemic mixture). After racemization, the (±) clopidogrel free base is isolated by solvent evaporation, and extraction using a mixture of dichloromethane and water. The dichloromethane layer contains the (±)clopidogrel base and aqueous layer contains the resolving agent (camphor sulphonic acid) and both are recovered and recycled. A particularly important aspect of this process of invention is that it avoids the isolation of (R) clopidogrel base from the diasteriomeric salt and directly converts it to the (±) clopidogrel base.

Finally, the dextro clopidogrel free base obtained above is converted to hydrogen sulphate salt in its two crystalline polymorphs, 'Form I' and 'Form II' by a reproducible process on large scale.

Large scale production of these two crystalline Forms according to the process described in the '915 patent resulted in Form II or a mixture or contaminated with either form at a higher percentage. Also the improved process of '443 patent application resulted in scale-up problems on large scale due to lump formation and semi-solid/sticky nature of the product at lower temperature and converts to more stable 'Form II'. Also encountered problems in maintaining precise control of temperature at different set points as stated in the '443 patent on large scale production.

This lead us to find suitable solvents or conditions where these problems are minimized and ensure reproducibility of Form I and II, particularly Form I without contamination of other forms. This research has led to an efficient process where Form I and Form II can be produced reliably from a single solvent or mixture of solvents.

Accordingly, the present invention provides a process for preparing polymorph Form I of clopidogrel hydrogen sulphate comprising dissolving the (+)clopidogrel base in solvents like methyl propyl ketone, methyl isopropyl ketone, diethyl ketone or mixture thereof, or mixture of ethyl acetate and methyl propyl ketone or mixture of ethyl acetate and methyl isopropyl ketone, or mixture of ethyl acetate and diethyl ketone; cooling to a temperature of −10° C. to 10° C.; adding concentrated sulphuric acid (98%, d=1.84) by maintaining the temperature at in the range of −10 to 20° C.; raising to a temperature of 10° C. to 15° C. and maintaining for 5 to 7 hours; further raising to a temperature of 28° to 30° C. and maintaining for a period of 7 to 10 hours and filtering the crystals obtained.

The mixture of ketone solvents include mixture of methyl propyl ketone and methyl isopropyl ketone, mixture of methyl propyl ketone and diethyl ketone, mixture of methyl isopropyl ketone and diethyl ketone, in all proportions.

In a further embodiment, the present invention provides a process for preparing polymorph Form I of clopidogrel hydrogen sulphate from ethyl acetate comprising the steps of dissolving the (+)clopidogrel base in ethyl acetate, cooling to a temperature of 18° C., adding concentrated sulphuric acid with or without maintaining temperature at 18°, raising to a temperature of 28° to 30° C. and maintaining for a period of 7 to 10 hours and filtering the crystals obtained.

In the process, in ethyl acetate, the temperature range of 18° to 30° C. gave Form I reproducibly on a large scale. Within this temperature range an easily dispersible mass is obtained and slight imbalance of temperature is well tolerated to give Form I consistently.

In both the cases, in the process for Form I, the preferred concentration of sulphuric acid was in the range of 90% to 98% and the molar ratios were in the range of 1 to 1.1 with respect to the (+) clopidogrel base. The most preferred concentration of sulphuric acid used in the salt formation was 96%.

In a preferred embodiment of the process, the exotherm of sulphuric acid addition is controlled by cooling and maintaining the temperature in between 18° to 24° C. in case of solvent ethyl acetate; and cooling and maintaining the temperature in between −10 to 10° C. in case of solvents methyl propyl ketone, methyl isopropyl ketone, diethyl ketone or their mixture thereof, or mixture of ethyl acetate and methyl propyl ketone or mixture of ethyl acetate and methyl isopropyl ketone, or mixture of ethyl acetate and diethyl ketone.

The Form I so obtained was confirmed by PXRD, DSC and FTIR without any detectable quantity of Form II or other polymorphic Forms with respect to the standard Form I PXRD pattern as described in '915 patent.

In another aspect, Form II crystals of (+) clopidogrel hydrogen sulphate is prepared from the same solvent ethyl acetate comprising steps of dissolving (+) clopidogrel base in the solvent, heating to a temperature of 45° C., adding concentrated sulphuric acid, stirring the reaction mixture at 45° C. to 50° C. for a period of 1 hour, cooling to 30° C. and continue stirring for a period of 4 to 7 hours to effect the complete crystallization.

In the process, the preferred concentration of sulphuric acid was in the range of 90% to 98% and the molar ratios were in the range of 1.0 to 1.1 with respect to clopidogrel base. The most preferred concentration of sulphuric acid used in the salt formation was 96%.

The Form II obtained by the process of the invention was confirmed by PXRD, DSC and FTIR and found to be identical with it disclosed in the '915 patent without any detectable contamination of Form I.

In yet another aspect, Form II of clopidogrel is prepared from ethyl acetate at a lower temperature of 5° to 15° C. comprising the steps of dissolving (+) clopidogrel base in ethyl acetate at 25° to 30° C., cool to 5° to 15° C. and mixing with conc. sulphuric acid at the said temperature, maintaining the mass under stirring for a period of 8 to 10 hours at 5 to 15° C. to yield crystals of clopidogrel Form II. The crystals obtained are filtered and dried and is identified as Form II by PXRD, FTIR and DSC without detectable contamination of Form I.

To our surprise the crystal form obtained at temperature below 15° C. and above 40° C. process conditions are the stable Form II crystals, while the temperature range of 18° to 30° C. processing conditions invariably yielded crystal Form I of clopidogrel hydrogen sulphate.

In another embodiment, the present invention provides a process for the preparation of Form II crystals of clopidogrel hydrogen sulphate from isopropyl alcohol comprising steps of dissolving clopidogrel base in solvent, adding concentrated sulphuric acid at a temperature of 28° to 30° C., stirring to effect complete crystallization for a period of 12 to 15 hours, filter and dry the crystals. The crystal form is identified equivalent to Form II. This solvent system (isopropyl alcohol) is, however, known to give Form IV.

In a preferred embodiment of the process the concentrated sulphuric acid is added as a solution in isopropyl alcohol.

The present invention also provides a process for the preparation of Form II of clopidogrel hydrogen sulphate from tetrahydrofuran comprising steps of dissolving clopidogrel base in solvent, cooling the reaction mass to a temperature of 10° to 15° C.; adding concentrated sulphuric acid at a temperature of 10° to 15° C., stirring to effect complete crystallization for a period of 6 to 8 hours, filter and dry the crystals. The crystal form is identified equivalent to Form II.

The following examples further illustrate the present invention but are not construed limiting in any manner to the scope of the invention as substantially described.

EXAMPLES

Example 1

One Pot Process for 4,5,6,7-tetrahydrothieno(3,2-c)pyridine Hydrochloride 100 gm. of 2-thienylethylamine was charged in a 1 liter reaction vessel equipped with a dean stark assembly for azeotropic removal of water. Dichloroethane (600 ml.) was added and the mixture stirred for 5 minutes. 26.4 gm. paraformaldehyde was added and the reaction mass was heated to reflux. Water formed in the reaction was continuously removed. After 4 hours the reaction mass was cooled to 30° C. and 133 ml. of 6.6N hydrochloric acid solution in dimethyl formamide was added. The reaction mass was heated to 70° C. for 4 hours. The reaction cooled to 15° C. and filtered under suction and washed with dichloroethane. The solid obtained was dried in oven at 50° C. 124 gm (90%) of 4,5,6,7-tetrahydrothieno(3,2-c)pyridine hydrochloride are obtained.

Example 2

Clopidogrel Base and Clopidogrel Hydrogen Sulphate (Dichloroethane as Solvent)

50 gm. 4,5,6,7-tetrahydrothieno(3,2-c)pyridine hydrochloride was charged in 1 liter reaction vessel. 150 ml. dichloroethane was added and stirred for 5 minutes. 75 gm. of methyl-1-bromo-(2-chlorophenyl)acetate and 80 ml. triethyl amine was added. Stirred at 25° C. for 1 hour and then heated to reflux for 4 hours. The reaction mixture cooled to room temperature and quenched in water. The organic layer was washed with water, and distilled the dichloroethane to obtain clopidogrel base as an oil.

This clopidogrel base was dissolved in 300 ml. acetone and mixed with 17.5 ml. Conc. Sulphuric acid under cooling. The precipitated pure Clopidogrel hydrogen sulphate was filtered and washed with acetone. The precipitate was dried in an oven at 50° C. and 105 gm.(88%) Clopidogrel hydrogen sulphate was obtained.

Example 3

Clopidogrel Base and Clopidogrel Hydrogen Sulphate (Water and Dichloroethane as Reaction Medium)

50 gm. of 4,5,6,7-tetrahydrothieno(3,2-c)pyridine hydrochloride was charged in 1 liter reaction vessel containing 500 ml. water and 75.4 gm. sodium carbonate and stirred for 1 hour. 75 gm. of methyl-1-bromo-(2-chlorophenyl) acetate in 250 ml. dichloroethane was added, stirred at 25° C. for 8 hours. The organic layer was separated and washed with water, and distilled the dichloroethane to obtain Clopidogrel base as an oil.

This was dissolved in acetone (300 ml.), cooled to 0-5° C. and mixed with 17.5 ml. conc. Sulphuric acid under cooling. The precipitated pure Clopidogrel hydrogen sulphate was filtered and washed with acetone. The precipitate was dried in an oven at 50° C. The 105 gm. (88%) Clopidogrel hydrogen sulphate was obtained.

Example 4

One-Pot Process for Clopidogrel Hydrogen Sulphate from Thienoethylamine 100 gm. of 2(2-thienyl)ethylamine was charged in a reaction vessel equipped with a dean-stark assembly for azeotropic removal of water. Dichloroethane (600 ml.) was added and the mixture stirred for 5 minutes. 26.4 gm. paraformaldehyde was added and the reaction mass was heated to reflux. Water formed in the reaction was continuously removed in 4 hours. The reaction mass was cooled to 30° C. and 133 ml. of 6.6 N hydrochloric acid solution in dimethyl formamide was added. The reaction mass was heated at 70° C. for 4 hours. The reaction cooled to 25° C. and an aqueous solution of sodium carbonate (prepared from 1400 ml. water and 208 gms sodium carbonate) was added. The mixture was stirred for 1 hour and a solution of 206.7 gm. of methyl-1-bromo-(2-chlorphenyl) acetate in 690 ml. dichloroethane was added. The reaction mass stirred at room temperature for 9 hours and the aqueous layer is discarded. The organic layer washed with water and dichloroethane was evaporated. To the oil left in the reaction vessel, 825 ml acetone was added and stirred for 1 hour. The mass cooled to 0 to 5° C. and 48 ml. conc. Sulphuric acid was added. The mixture was further stirred for 4 hours. The precipitated crystals filtered off under suction and the pure Clopidogrel hydrogen sulphate was dried in oven at 50° C. to get 280.5 gm (85%).

Example 5

(S)(+) Clopidogrel Base 93.0 gm (0.28 mole) of racemic base methyl-2-(2-chlorophenyl)-2-(4,5,6,7-tetrahydrothieno [3,2-c] pyridin-5-yl) acetate was charged in 550 ml mixture of acetone and dichloromethane solvent. 73.8 gm (0.31 mole) levo-camphor-10-sulphonic acid was added in the solution. The clear solution was stirred overnight at 30±2° C. and cooled the reaction mass to −2 to 3°C. The crystals obtained was filtered and washed with acetone and dried at room temperature under vacuum to give 61 gm of diasteriometric salt of (S)clopidogrel. The yield obtained is 76.0% on the basis of the starting racemate charged. The crystals have $[\alpha]_D^{20}$+25·25 (c=1.89%, methanol); HPLC (AGP$^{(R)}$ column) assay=99.65%.

The diasteriomeric salt (60 gm) obtained above was dissolved in 240 ml water containing 16.8 gms of Sodium bicarbonate and 240 ml ethyl acetate was added and stirred for a period of 2 hours at room temperature. The organic layer was separated and washed with water and evaporated to give 35.35 gm of (+)-(S)-Clopidogrel base as an oil.

Example 6

(S)(+) Clopidogrel Base 93.0 gm (0.28 mole) of racemic base methyl-2-(2-chlorophenyl)-2-(4,5,6,7-tetrahydrothieno [3,2-c] pyridin-5-yl) acetate is charged in 550 ml mixture of acetone and toluene. 73.8 gm (0.31 mole) levo-camphor-10-sulphonic acid is added to the solution. The clear solution is stirred overnight at 30±2° c. The reaction mass is cooled to −2 to 3° C. The crystals obtained is filtered and washed with acetone and dried under reduced pressure. The yield obtained is 80% on the basis of the starting racemate charged. The crystals have $[\alpha]_D$20+24.49(c=1.89%, methanol); HPLC(AGP$^{(R)}$ column) assay=99.285%. The camphor sulphonate salt was further cleaved to obtain (S)(+)clopidogrel base as in example 5.

Example 7

Clopidogrel base (5.79 kg) was dissolved in methyl propyl ketone (37 liter) at room temperature. This mixture was cooled to −10° C. and concentrated sulphuric acid (96%, density=1.83) was added (1.02 liter) maintaining temperature −10° to 0° C. while addition. The reaction mass was stirred for 1.0 hour and warmed slowly to 10 to 15° C. in 30 to 45 minute. The formed crystals were stirred for 7 hour. The reaction mass temperature was further raised to 28 to 30° C. and maintained for 8.0 hour. The solid obtained was filtered under suction and washed with methyl propyl ketone, and dried in oven at 48° C. for 3 hour. The solid after drying weighed 6.82 kg (90%) was Form I clopidogrel hydrogen sulphate (PXRD pattern incorporated: FIG. 1)

Example 8

Clopidogrel base (5.79 kg) was dissolved in methyl isopropyl ketone (37 liter) at room temperature. This mixture was cooled to −10° C. and concentrated sulphuric acid (96%, density=1.83) was added (1.02 liter) maintaining temperature −10° to 0° C. while addition. The reaction mass was stirred for 1.0 hour and warmed slowly to 10 to 15° C. in 30 to 45 minutes. The formed crystals were stirred for 7 hour. The reaction mass temperature was further raised to 28 to 30° C. and maintained for 8.0 hour. The solid obtained was filtered under suction and washed with methyl isopropyl ketone, and dried in oven at 48° C. for 3 hour. The solid after drying weighed 6.82 kg (90%) was Form I clopidogrel hydrogen sulphate (PXRD pattern is identical with FIG. 1).

Example 9

Clopidogrel base (5.79 kg) was dissolved in ethyl acetate (30 liter) at room temperature. This mixture was cooled to 18° C. and concentrated sulphuric acid (96%, density=1.83) was added (1.02 liter) maintaining temperature 18° to 20° C. while addition. The reaction mass was stirred for 30 minutes and warmed slowly to 28° to 30° C. in 30 to 40 minute. The formed crystals were stirred for 8 hour. The solid obtained was filtered under suction and washed with ethyl acetate, and dried in oven at 40° C. for 3 hour. The solid after drying weighed 6.7 kg (88%) was Form I clopidogrel hydrogen sulphate (PXRD pattern is identical with FIG. 1).

Example 10

Figure 2:
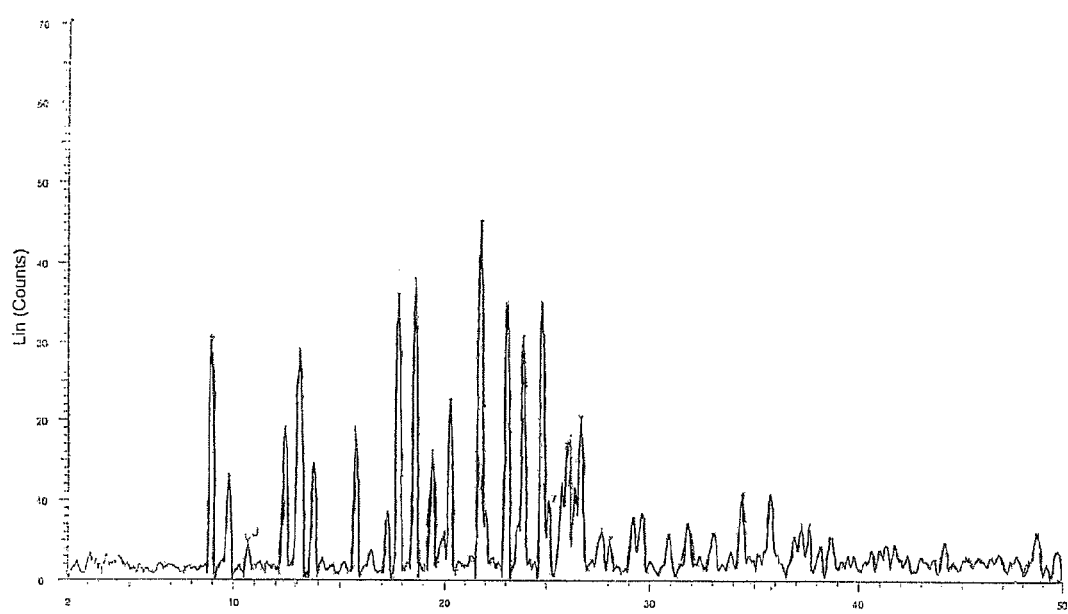
FIG. 2 represents Powder X-Ray diffraction pattern (PXRD) of clopidogrel hydrogen sulphate Form II prepared according to example 10 of the present invention.
Figure 3:
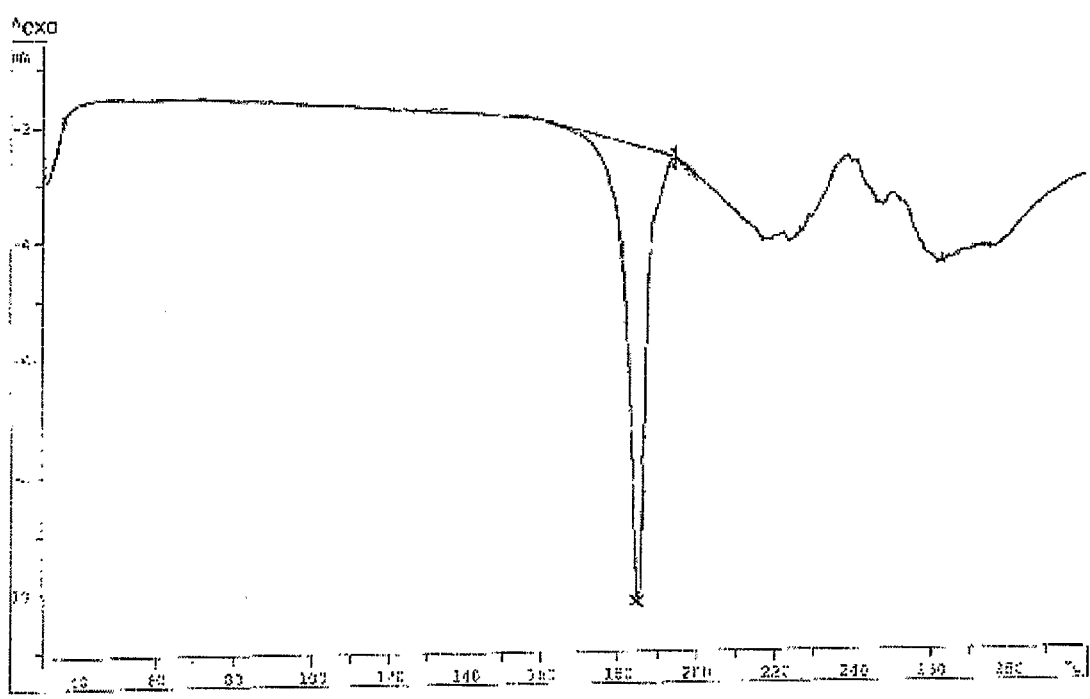
FIG. 3 represents Differential Scanning Calorimetry record of Form I of clopidogrel hydrogen sulphate prepared according to example 7 of the present invention.
Figure 4:
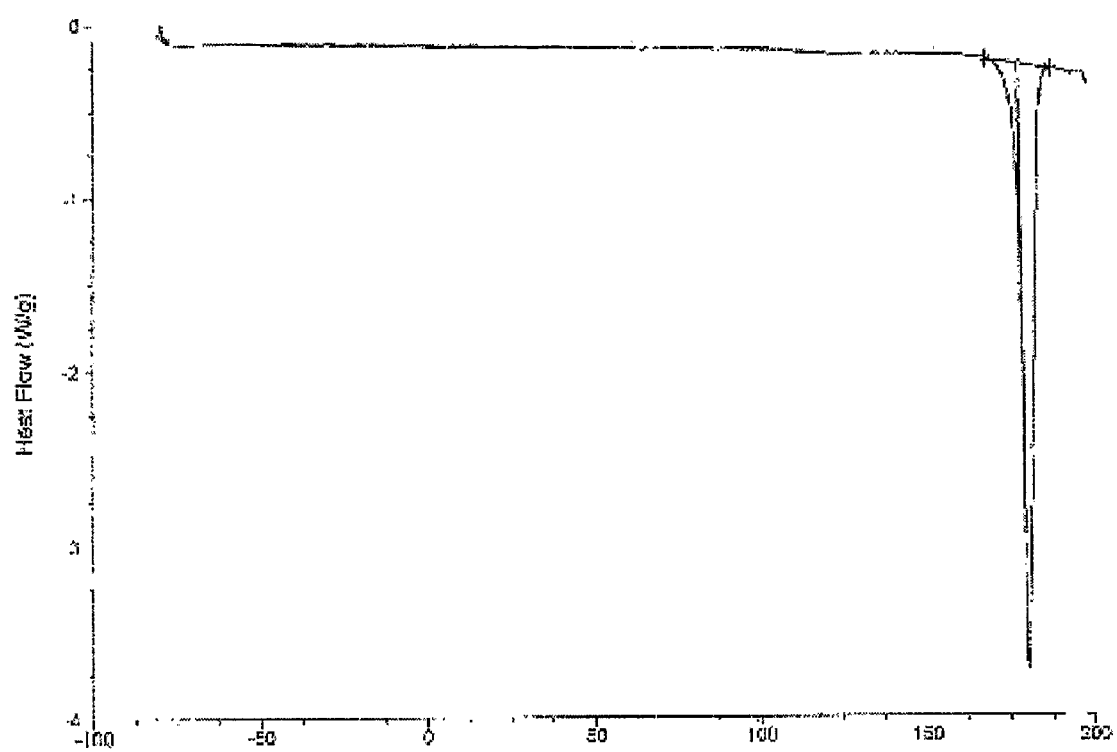
FIG. 4 represents Differential Scanning Calorimetry record of Form II of clopidogrel hydrogen sulphate prepared according to example 10 of the present invention.
Figure 5:
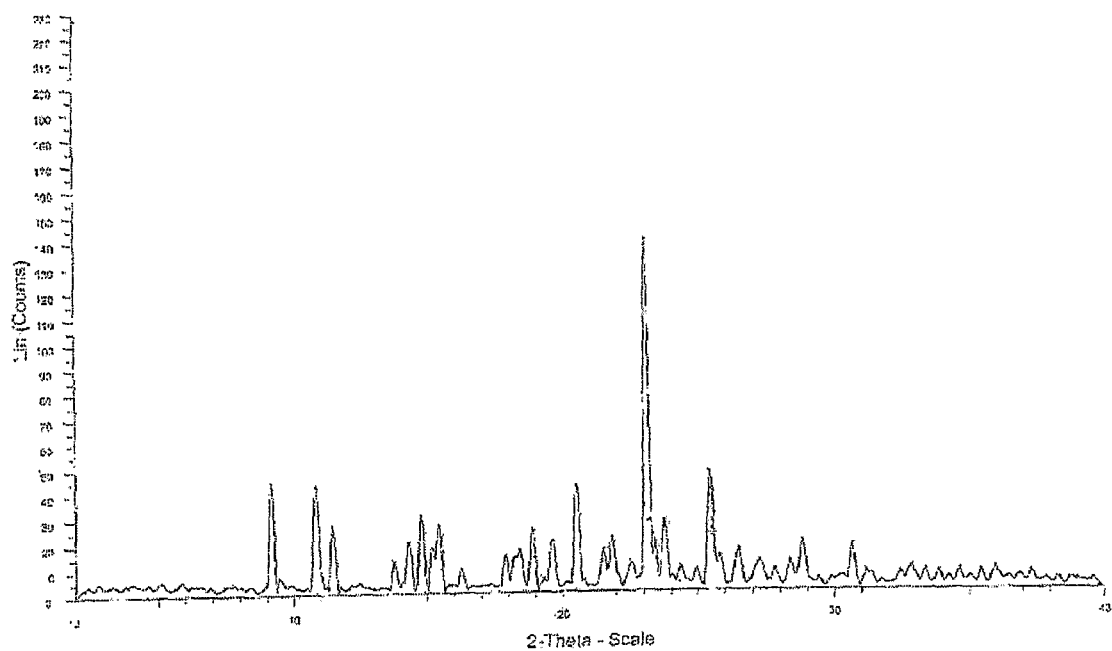
FIG. 5 represents Powder X-Ray diffraction pattern (PXRD) of clopidogrel hydrogen sulphate Form I standard as given in '915 patent.
Figure 6:
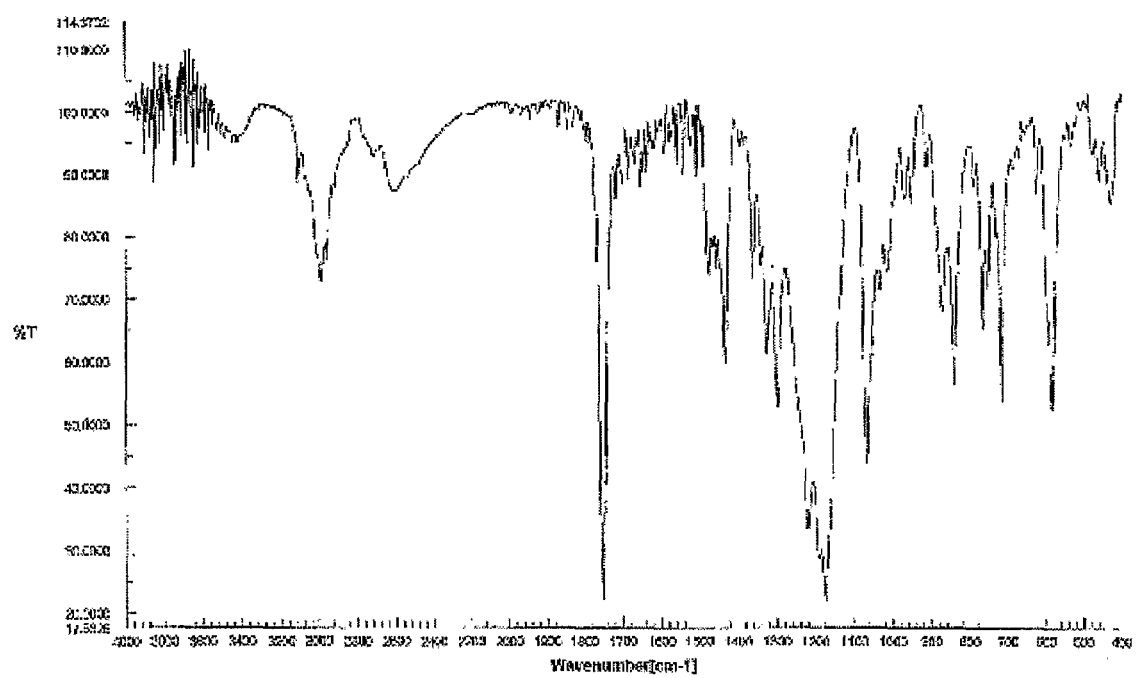
FIG. 6 represents the spectrogram obtained by Fourier Transform Infra Red spectrometry (FTIR) of clopidogrel hydrogen sulphate Form I prepared according to example 7 of the present invention
Figure 7:
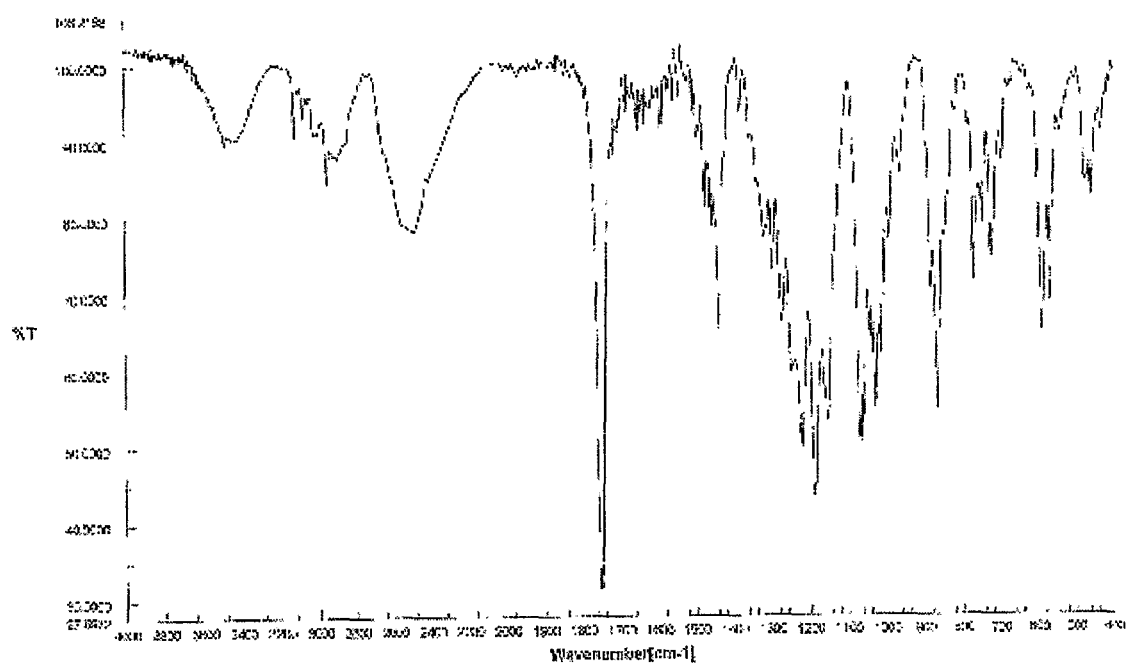
FIG. 7 represents spectrogram obtained by Fourier Transform Infra Red spectrometry (FTIR) of clopidogrel hydrogen sulphate Form II prepared according to example 10 of the present invention.
Figure 8:
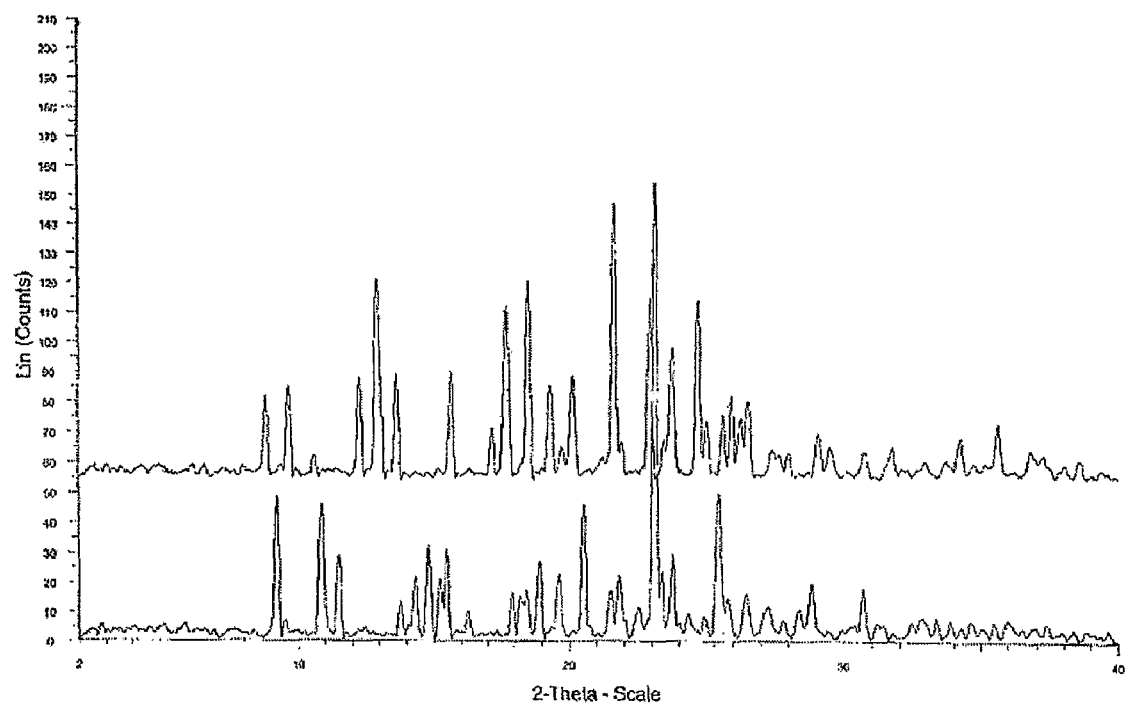
FIG. 8 represents an overlay of powder x-ray diffraction pattern (PXRD) of clopidogrel hydrogen sulphate crystalline Form I and Form II.

Clopidogrel base (5.79 kg) was dissolved in ethyl acetate (30 liter) at room temperature. This mixture was heated to 45° C. and concentrated sulphuric acid (96%, density=1.83) was added (1.02 liter). The reaction mass was stirred for 30 minutes at 45° to 50° C. The formed crystals were cooled to 30° C. in one hour and stirred for 4 hour. The solid obtained was filtered under suction and washed with ethyl acetate, and dried in oven at 48° C. for 3 hour. The solid after drying weighed 6.5 kg (86%) and identified as pure clopidogrel hydrogen sulphate Form II ( PXRD pattern incorporated FIG. 2)

Example 11

Clopidogrel base (5.79 kg) was dissolved in ethyl acetate (30 liter) at room temperature. This mixture was cooled to 20°

C. and concentrated sulphuric acid (98%, density=1.84) was added (1.02 liter). The temperature rose to 28° C. while addition and the reaction mass was stirred for 10 hour at 28° to 30° C. The solid obtained was filtered under suction and washed with ethyl acetate, and dried in oven at 40° C. for 3 hour. The solid after drying weighed 6.8 kg (89.6%) and identified as pure clopidogrel hydrogen sulphate Form I (PXRD pattern is identical with FIG. 1).

Example 12

Clopidogrel base (7.25 kg) was dissolved in isopropyl alcohol (62.5 liter) at room temperature. This mixture was maintained at 28° to 30° C. and concentrated sulphuric acid solution in isopropyl alcohol (prepared by mixing 1.14 liter concentrated sulphuric acid and 43.5 liter isopropyl alcohol) was added. The reaction mass was stirred for 12 hour at 28° to 30° C. The solid obtained was filtered under suction and washed with ethyl acetate, and dried in oven at 48° C. for 3 hours. The solid after drying weighed 7.6 kg (80%) and identified as pure clopidogrel hydrogen sulphate Form II ( PXRD pattern as in example 4).

Example 13

Clopidogrel base (5.79 kg) was dissolved in tetrahydrofuran (30 liter) at room temperature. This mixture was cooled to 10° to 15° C. and concentrated sulphuric acid (80%) solution 1.4 liter was added while maintaining the temperature under cooling. The reaction mass was stirred for 8 hour at 13° to 15° C. The solid obtained was filtered under suction and washed with tetrahydrofuran, and dried in oven at 48° C. for 3 hour. The solid after drying weighed 5.9 kg (78%) and identified as pure clopidogrel hydrogen sulphate Form II (PXRD pattern as in example 4).

Example 14

Clopidogrel base (5.79 kg) was dissolved in ethyl acetate (30 liter) at room temperature. This mixture was cooled to 5° C. and concentrated sulphuric acid (98%, density=1.84) was added (1.02 liter) while maintaining the temperature at 5° to 10° C. and the reaction mass was stirred for 3 hour at 10° to 15° C. and maintained for 10 to 12 hour at 24° C. The solid obtained was filtered under suction and washed with ethyl acetate, and dried in oven at 48° C. for 3 hour. The solid after drying weighed 6.9 kg (90%) and identified as pure clopidogrel hydrogen sulphate Form II ( PXRD pattern was identical as in example 4)

Example 15

Clopidogrel base (5.79 kg) was dissolved in ethyl acetate (30 liter) at room temperature. This mixture was cooled to 10° C. and concentrated sulphuric acid (98%, density=1.84) was added (1.02 liter) while maintaining the temperature at 10° to 15° C. and the reaction mass was stirred for 10 hour at 15° C. The solid obtained was filtered under suction and washed with ethyl acetate, and dried in oven at 48° C. for 3 hours. The solid after drying weighed 6.7 kg (89.6%) and identified as pure clopidogrel hydrogen sulphate Form II (PXRD pattern was identical as in example 4).

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

We claim:

1. An process for making Form I crystals of (+)-(S)-clopidogrel hydrogen sulphate of Formula IB comprising the steps of:

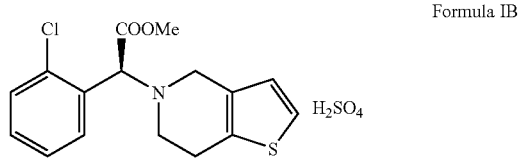

Formula IB i) dissolving methyl (+)-(S)-α-(2-chlorophenyl)-4,5,6,7-tetrahydrothieno [3,2-C]pyridine-5-acetate ((+)-(S)-clopidogrel base) in a solvent selected from methyl propyl ketone, methyl isopropyl ketone, diethyl ketone, mixture of ketone solvents, ethyl acetate—methyl propyl ketone mixture, ethyl acetate-methyl isopropyl ketone mixture, and ethyl acetate-diethyl ketone mixture;
ii) cooling said clopidogrel base solution;
iii) adding sulphuric acid to said cooled solution to form a salt mixture;
iv) maintaining said salt mixture to precipitate (+)-(S)-clopidogrel hydrogen sulphate in Form I; and
v) recovering said crystals of Form I.

2. The process of claim 1, wherein said mixture of ketone solvents are mixtures of methyl propyl ketone and methyl isopropyl ketone, mixture of methyl propyl ketone and diethyl ketone, or mixture of methyl isopropyl ketone and diethyl ketone.

3. The process of claim 1, wherein step ii) involves cooling to a temperature range of –10 to 20° C.

4. The process of claim 1, wherein step iii) is carried out while maintaining reaction solution temperature at –10 to 10° C.

5. The process of claim 1, wherein the solution is seeded with Form I prior to addition of sulphuric acid.

6. The process of claim 1, wherein the mixture of step iv) is maintained at a temperature range of 10° to 30° C.

7. The process of claim 6, wherein the mixture of step iv) is maintained at 10° to 30° C. for 8 to 15 hours.

8. The process of claim 1, wherein the solvent is methylpropyl ketone.

9. The process of claim 1, wherein the solvent is methylisopropyl ketone.

10. The process of claim 1, wherein the solvent is ethyl acetate-methylpropyl ketone.

11. The process of claim 1, wherein the solvent is ethyl acetate-methylisopropyl ketone.

12. The process of claim 1, wherein the solvent is methyl propyl ketone and methyl isopropyl ketone.

* * * * *